United States Patent
Daignault et al.

(10) Patent No.: US 7,347,866 B2
(45) Date of Patent: Mar. 25, 2008

(54) MEDICAL STENT AND RELATED METHODS

(75) Inventors: Kenneth J. Daignault, Holden, MA (US); Alfred P. Intoccia, Amherst, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 515 days.

(21) Appl. No.: 10/385,209

(22) Filed: Mar. 10, 2003

(65) Prior Publication Data

US 2004/0181235 A1     Sep. 16, 2004

(51) Int. Cl.
    *A61M 29/00*   (2006.01)
(52) U.S. Cl. .............. 606/191; 606/198; 604/104
(58) Field of Classification Search ..... 623/23.64–23.7
    See application file for complete search history.

(56) References Cited

U.S. PATENT DOCUMENTS

| | | | |
|---|---|---|---|
| 3,397,699 A | 8/1968 | Kohl | |
| 3,938,529 A | 2/1976 | Gibbons | 128/349 |
| 3,951,153 A | 4/1976 | Leucci | 128/349 |
| 3,970,090 A | 7/1976 | Loiacono | 128/349 |
| 4,026,298 A | 5/1977 | Grausz | 128/349 |
| 4,148,319 A | 4/1979 | Kasper et al. | 128/349 |
| 4,149,539 A | 4/1979 | Cianci | 128/325 |
| 4,154,242 A | 5/1979 | Termanini | 128/349 |
| 4,198,984 A | 4/1980 | Taylor | 128/349 |
| 4,211,233 A | 7/1980 | Lin | 128/349 |
| 4,222,384 A | 9/1980 | Birtwell | 128/349 |
| 4,227,533 A | 10/1980 | Godfrey | 128/349 |
| 4,249,536 A | 2/1981 | Vega | 128/349 |
| 4,284,081 A | 8/1981 | Kasper et al. | 128/349 |
| 4,501,580 A | 2/1985 | Glassman | 604/43 |
| 4,553,959 A | 11/1985 | Hickey et al. | 604/96 |
| 4,660,560 A | 4/1987 | Klein | 128/344 |
| 4,778,461 A * | 10/1988 | Pietsch et al. | 623/2.19 |
| 4,813,935 A | 3/1989 | Haber et al. | 604/99 |
| 4,861,337 A | 8/1989 | George | 604/96 |
| 4,955,859 A * | 9/1990 | Zilber | 604/544 |
| 4,973,301 A * | 11/1990 | Nissenkorn | 604/8 |
| 4,994,066 A | 2/1991 | Voss | 606/108 |
| 5,002,558 A | 3/1991 | Klein et al. | 606/192 |
| 5,007,898 A | 4/1991 | Rosenbluth et al. | 604/54 |
| 5,019,102 A | 5/1991 | Hoene | 623/12 |

(Continued)

FOREIGN PATENT DOCUMENTS

FR    2 747 574    10/1997

(Continued)

OTHER PUBLICATIONS

International Search Report for International Application No. PCT/US2004/006397, dated Apr. 8, 2004.

*Primary Examiner*—Glenn K. Dawson

(57) ABSTRACT

A stent includes a conduit defining a lumen; a first malecot adjacent the conduit, where the first malecot includes at least two members having at least one slit therebetween and where the at least one slit is in fluid communication with the lumen; and a second malecot including an annular structure surrounding and protruding from the conduit. A method for placing a stent includes inserting into a patient a stent and a stylet disposed within the stent, where the stylet includes an expandable member, expanding the expandable member, seating the stent, and removing the expandable member.

8 Claims, 9 Drawing Sheets

U.S. PATENT DOCUMENTS

| | | | |
|---|---|---|---|
| 5,030,227 A | 7/1991 | Rosenbluth et al. | 606/192 |
| 5,059,169 A | 10/1991 | Zilber | 604/8 |
| 5,167,614 A | 12/1992 | Tessmann et al. | 604/8 |
| 5,178,148 A | 1/1993 | Lacoste et al. | 128/660.03 |
| 5,203,773 A * | 4/1993 | Green | 604/104 |
| 5,269,802 A | 12/1993 | Garber | 606/191 |
| 5,306,241 A | 4/1994 | Samples | 604/54 |
| 5,312,430 A | 5/1994 | Rosenbluth et al. | 606/192 |
| 5,322,501 A * | 6/1994 | Mahmud-Durrani | 604/544 |
| 5,518,498 A | 5/1996 | Lindenberg et al. | |
| 5,667,486 A | 9/1997 | Mikulich et al. | 604/8 |
| 5,718,686 A | 2/1998 | Davis | 604/101 |
| 5,752,971 A | 5/1998 | Rosenbluth et al. | 606/192 |
| 5,785,641 A | 7/1998 | Davis | 600/30 |
| 5,830,179 A | 11/1998 | Mikus et al. | |
| 5,836,913 A * | 11/1998 | Orth et al. | 604/107 |
| 5,865,815 A | 2/1999 | Tihon | 604/280 |
| 5,916,195 A | 6/1999 | Eshel et al. | 604/96 |
| 5,964,732 A | 10/1999 | Willard | 604/117 |
| 5,971,967 A | 10/1999 | Willard | 604/264 |
| 6,004,290 A | 12/1999 | Davis | 604/96 |
| 6,033,413 A | 3/2000 | Mikus et al. | 606/108 |
| 6,053,897 A | 4/2000 | Sachse | 604/264 |
| 6,168,622 B1 * | 1/2001 | Mazzocchi | 623/1.2 |
| 6,221,060 B1 | 4/2001 | Willard | 604/264 |
| 6,254,570 B1 | 7/2001 | Rutner et al. | 604/101.02 |
| 6,258,060 B1 | 7/2001 | Willard | 604/117 |
| 6,929,663 B2 * | 8/2005 | Rioux et al. | 623/23.64 |
| 6,972,040 B2 * | 12/2005 | Rioux et al. | 623/23.66 |
| 6,981,964 B2 * | 1/2006 | Rioux et al. | 604/107 |
| 7,090,688 B2 * | 8/2006 | Nishtala et al. | 606/198 |
| 2001/0012950 A1 | 8/2001 | Nishtala et al. | 606/198 |
| 2002/0035391 A1 * | 3/2002 | Mikus et al. | 623/1.11 |
| 2002/0065476 A1 | 5/2002 | Whalen et al. | 600/587 |
| 2002/0107540 A1 * | 8/2002 | Whalen et al. | 606/192 |
| 2004/0176782 A1 * | 9/2004 | Hanse et al. | 606/129 |
| 2004/0220610 A1 * | 11/2004 | Kreidler et al. | 606/200 |

FOREIGN PATENT DOCUMENTS

| | | |
|---|---|---|
| WO | WO 98/26509 | 6/1998 |
| WO | WO 99/16499 A1 | 4/1999 |
| WO | WO 99/30635 | 6/1999 |
| WO | WO 02/058541 A2 | 8/2002 |

* cited by examiner

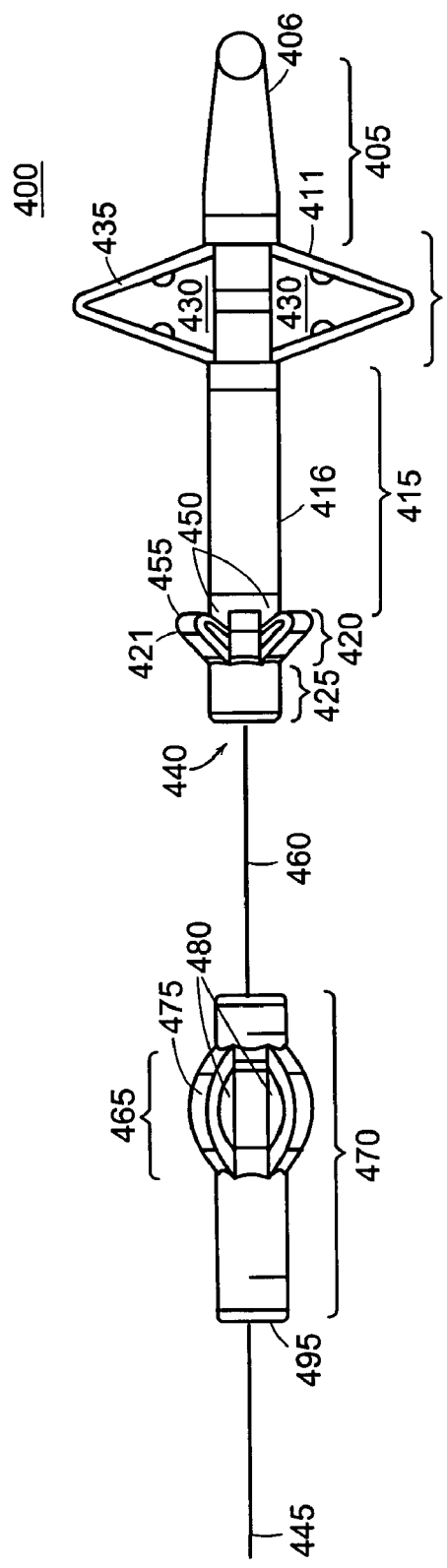
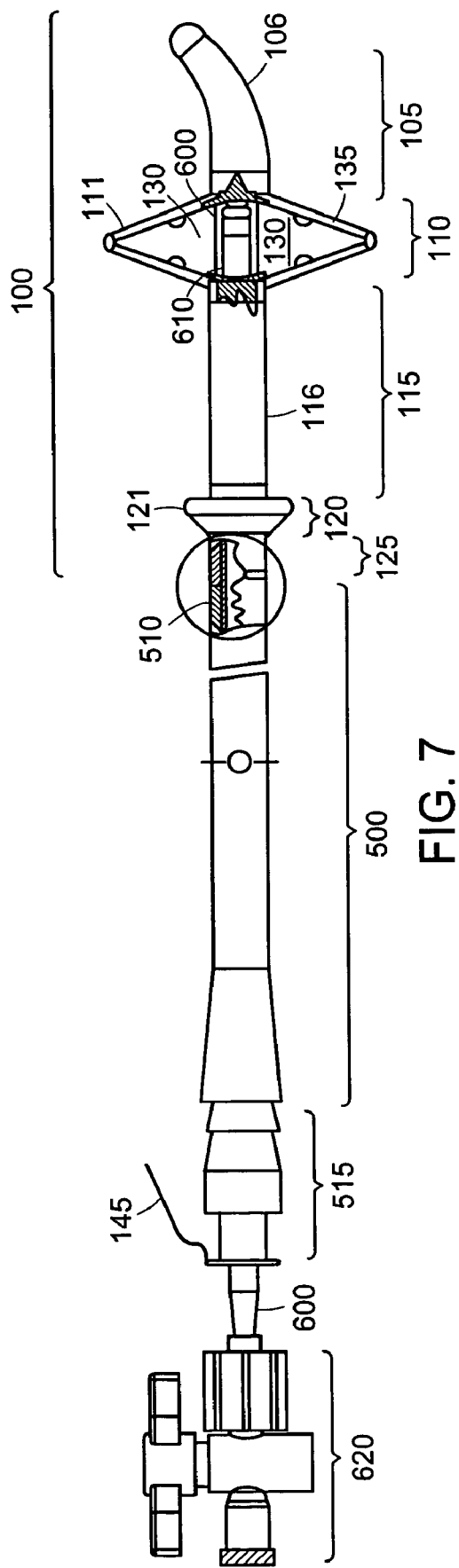
FIG. 6
FIG. 7

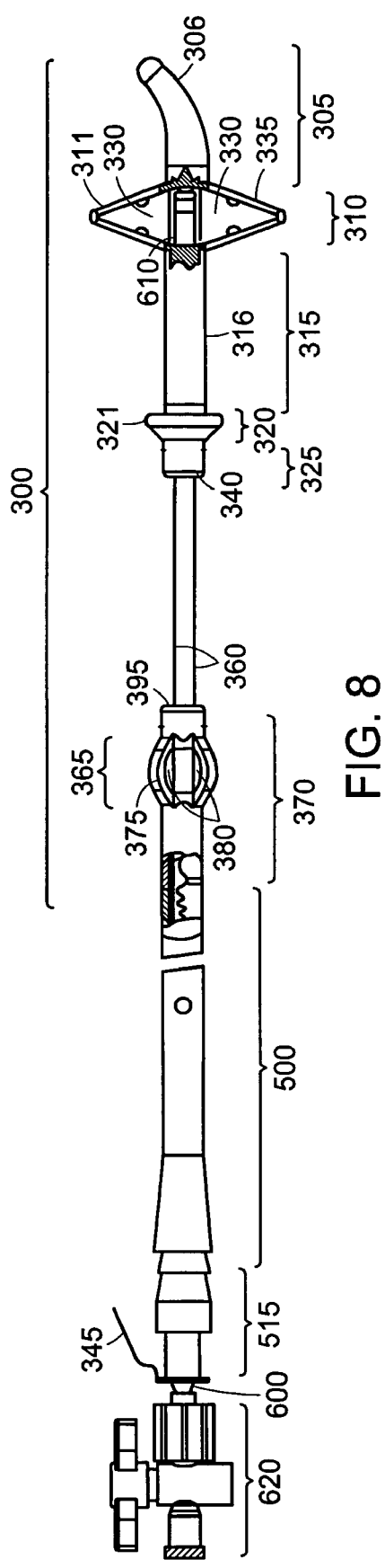
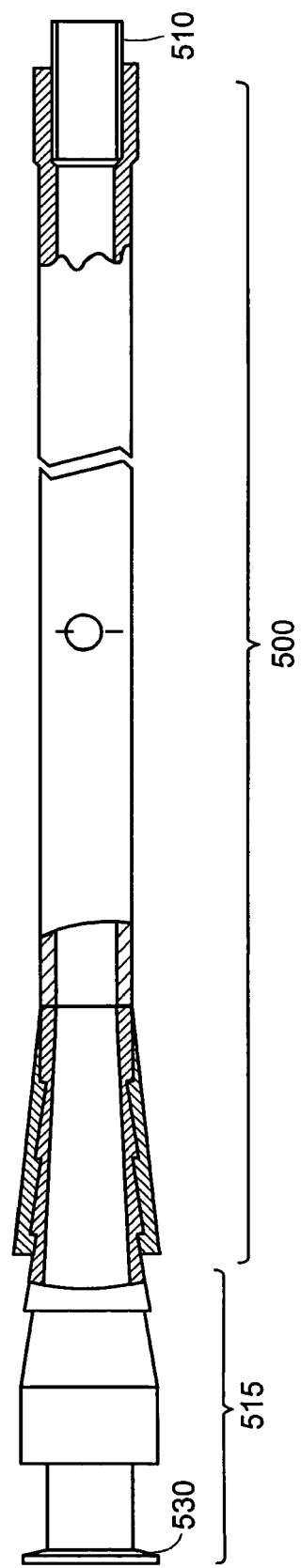
FIG. 8
FIG. 9

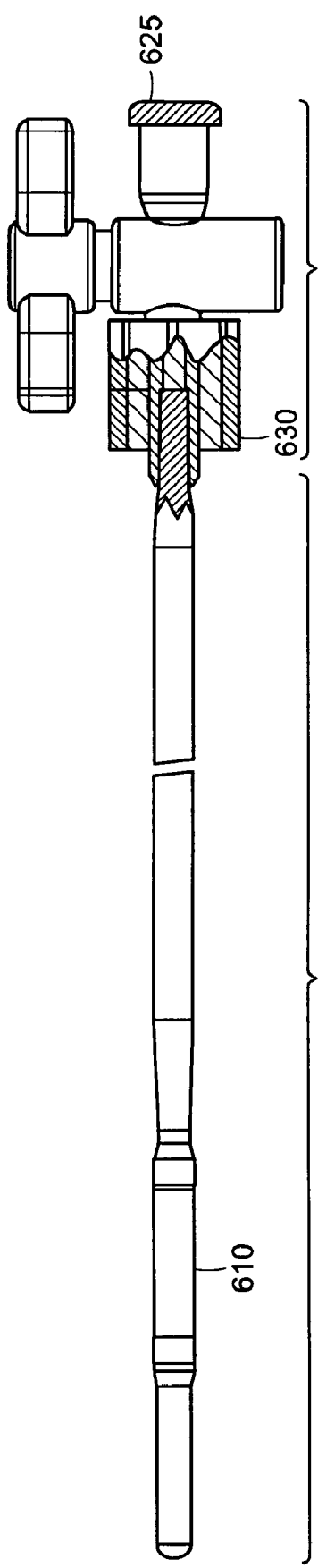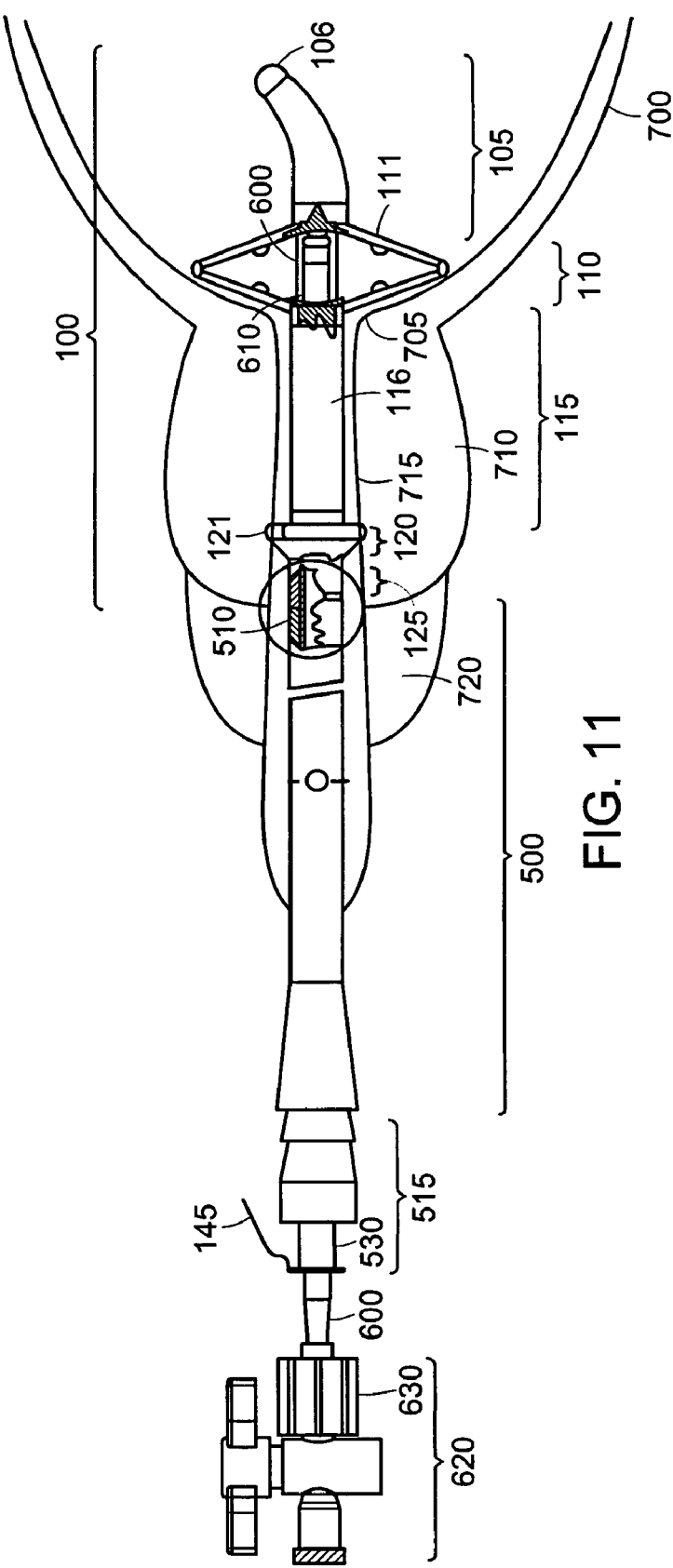

MEDICAL STENT AND RELATED METHODS

TECHNICAL FIELD

The present invention relates to medical stents and related methods. More specifically, the invention relates to medical stents having structures to anchor the stent within, for example, the urethra of a patient.

BACKGROUND

A patient can suffer from urinary retention, possibly caused by obstruction within the prostatic urethra such as that associated with Benign Prostatic Hyperplasia (BPH). As a result, urine within the bladder may need to be drained from the bladder and through the urethra. One way to accomplish such drainage is to use a medical device that conveys the urine through a lumen, while maintaining the patency of the prostatic urethra. Such devices include stents and catheters. Existing stents often migrate distally or proximally within the urethra, thereby impairing proper function of the stent in relieving the prostatic obstruction and/or impairing normal function of the external striated sphincter in controlling urine discharge from the urethra. Existing stents and catheters also can be uncomfortable for the patient. Furthermore, existing stents typically require ultrasound, cytoscopy, or other means to ensure that the device is properly positioned. Even with assisted placement techniques, it can be difficult to ensure that the stent is properly positioned. For example, ultrasound typically does not provide a clear picture of stent locations and cytoscopy typically cannot pass through the stent to assess proper distal placement.

SUMMARY OF THE INVENTION

The present invention provides medical stents for maintaining the patency of a prostatic urethra in order to facilitate drainage of urine and provides methods for placing such stents within the body of a patient. The design of the stent and the incorporated malecots according to the invention provides an effective and comfortable way to anchor the stent within the body and, in particular, a prostatic segment of the stent within the prostatic urethra. In addition, the expandable and collapsible nature of the malecots allows for easy insertion and removal of the stent within the urethra of a patient. Moreover, the implantation device in combination with the design of the stent provides a method for properly positioning the stent without having to perform additional procedures to ensure proper stent placement, simplifying stent placement.

One aspect of the invention relates to a stent including a conduit defining a lumen; a first malecot adjacent the conduit, where the first malecot includes at least two members having at least one slit therebetween, the at least one slit in fluid communication with the lumen; and a second malecot including an annular structure surrounding and protruding from the conduit. The aspect of the invention described above can have any of the following features. The first malecot can have a diameter larger than a diameter of the second malecot. At least one of the conduit, the first malecot, and the second malecot can be formed from a material having a durometer value less than about 60 on a Shore A scale. Alternatively, at least one of the conduit, the first malecot, and the second malecot can be formed from a material having a durometer value less than about 30 on a Shore A scale. At least one of the conduit, the first malecot, and the second malecot can include a silicone polymer. The at least two members can be capable of folding such that the size of the at least one slit is larger when the at least two members are in a first position than when the at least two members are in a second position. The annular structure can be disposed at an angle relative to the conduit. In addition, the annular structure can be enclosed. The conduit, first malecot, and second malecot can form a primary stent body, the primary stent body further connected to a third malecot. A spring can be disposed within the conduit. Furthermore, the spring can be disposed within a wall of the conduit.

Another aspect of the invention relates to a method of placing a stent in a patient including inserting into a patient a stent and a stylet disposed within the stent, where the stylet includes an expandable member, expanding the expandable member, seating the stent, and removing the expandable member from the patient. The aspect of the invention described above can have the following features. The stent can be inserted without the aid of a scope. The expandable member can be positioned within the stent. The expandable member can include a balloon. At least a portion of the stent can be positioned within a prostatic urethra of a patient. In addition, the stent can include a conduit adjacent to a malecot capable of moving between a first conformation and a second conformation. The stent can include a conduit defining a lumen; a first malecot adjacent the conduit, where the first malecot includes at least two members having at least one slit therebetween, the at least one slit in fluid communication with the lumen; and a second malecot including an annular structure surrounding and protruding from the conduit. The expandable member can be expanded within the first malecot. Alternatively, the stent can include a first conduit defining a lumen, the first conduit including at least one malecot selected from the group consisting of a malecot including at least two members having at least one slit therebetween where the at least one slit is in fluid communication with the lumen; and a malecot including an annular structure surrounding and protruding from the first conduit. The stent further includes a second conduit connected to the first conduit. The connection between the first and second conduit can traverse a sphincter in the patient.

Another aspect of the invention relates to a stent including a first conduit defining a lumen, the first conduit including at least one malecot selected from the group consisting of a malecot including at least two members having at least one slit therebetween where the at least one slit is in fluid communication with the lumen; and a malecot including an annular structure surrounding and protruding from the first conduit. The stent further includes a second conduit connected to the first conduit. The aspect of the invention described above can have the following features. The second conduit can include a malecot including at least two members having at least one slit in fluid communication with the lumen. The connection can include a connector suture.

BRIEF DESCRIPTION OF THE DRAWINGS

The foregoing and other objects, aspects, and advantages of the invention and the various features thereof may be more fully understood from the following description when read together with the accompanying drawings. In the drawings, like reference characters generally refer to the same parts throughout the different views. Also, the drawings are not necessarily to scale, emphasis instead generally being placed upon illustrating the principles of the technology.

FIG. 6 depicts a schematic rendering of a fourth embodiment of a urethral stent according to the invention.

FIG. 7 depicts a schematic rendering of the urethral stent of FIG. 1 and an associated implantation device.

FIG. 8 depicts a schematic rendering of the urethral stent of FIG. 4 and an associated implantation device.

FIG. 9 depicts a schematic rendering of an introducer sheath of the implantation device of FIGS. 7 and 8.

FIG. 10 depicts a schematic rendering of a stylet of the implantation device of FIGS. 7 and 8.

FIG. 11 depicts a schematic rendering of the urethral stent of FIG. 1 associated with the implantation device of FIG. 7, as placed within the body.

DESCRIPTION

The present invention provides medical stents for facilitating fluid drainage and methods for placing such stents within the body of a patient. For example, such stents are placed in the urethra to facilitate drainage of urine from a patient's bladder through the urethra. However, it should be understood that stents and methods according to the invention can be used in other body locations. For example, the stent may be placed within the ureter for use as a ureteral stent or, alternatively, may be placed within a bile duct for use as a biliary stent. Generally, stents according to the invention have an expandable distal malecot for placement within the bladder of a patient and an expandable proximal malecot for placement within or at the proximal end of the prostatic urethra. As used herein, "distal" refers to the end of the stent farthest away from a medical professional when placing the stent in a patient. By contrast, "proximal" refers to the end of the stent closest to a medical professional when placing the stent in a patient. The distal malecot, placed within the bladder neck, serves to prevent anterograde migration of the stent proximally into the urethra. The proximal malecot serves to prevent retrograde migration of the stent distally toward the bladder. In an alternative embodiment, the bulbar design, the stent has an additional bulbous urethral segment attached via sutures or other type of resilient connection to the previously described primary stent body. The suture or other type of resilient connector provides for normal functioning of the urethral sphincter while the stent is in place. The bulbous urethral segment also has an optional malecot for anchoring the segment within the urethra proximal to the urethral sphincter.

The design of the stent and the incorporated malecots according to the invention provides an effective and comfortable way to anchor the stent within the body. In addition, the expandable and collapsible nature of the malecots allows for easy insertion and removal of the stent within the urethra of a patient without the need for further assisted placement procedures such as cytoscopy or ultrasound. In general, malecots are structures that serve to retain stents according to the invention at a desired location. Several embodiments are disclosed herein. However, other designs that allow retention are envisioned. Furthermore, an implantation device in combination with the design of the stent provides a method for properly positioning the stent without having to perform additional procedures to ensure proper stent placement, simplifying stent placement.

Figure 1:
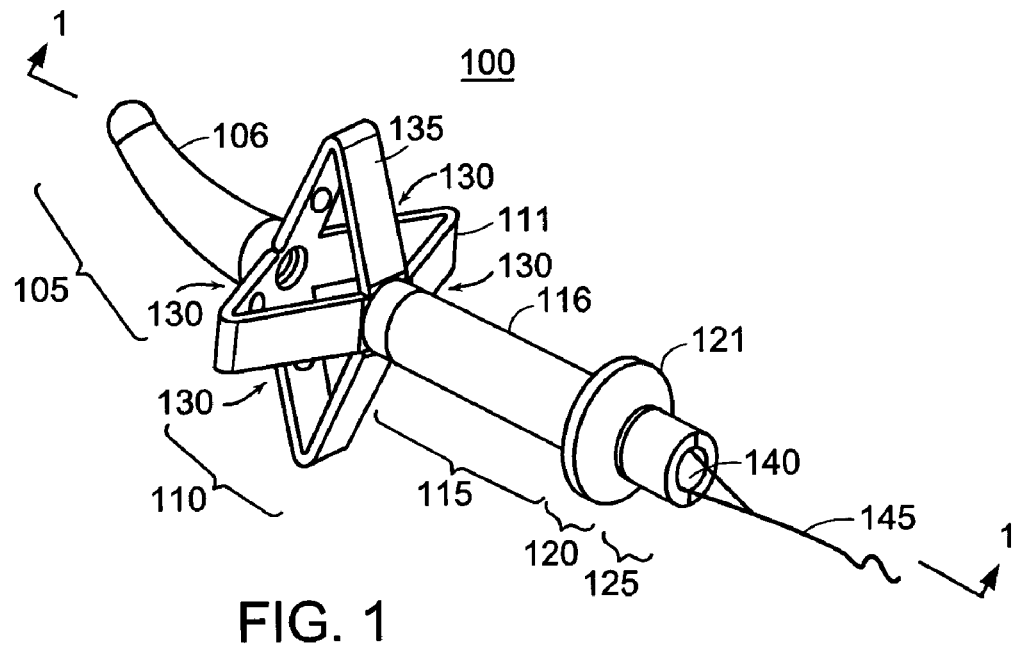
FIG. 1 depicts a schematic rendering of a first embodiment of a urethral stent according to the invention.
Figure 2:
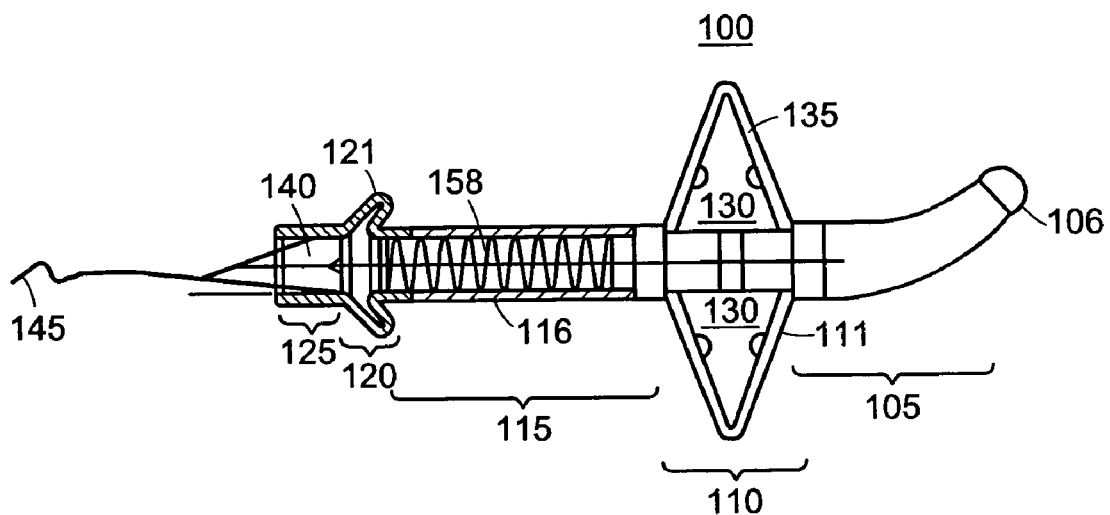
FIG. 2 depicts a schematic rendering of a cross section of the embodiment of the urethral stent of FIG. 1 taken along section line 1-1.

Referring to FIGS. 1 and 2, a schematic representation of one embodiment, a non-bulbar design, of a stent 100 according to the invention is shown. Generally, the stent 100 has five sections 105, 110, 115, 120, 125. A first section 105, located at the distal end of the stent 100, includes a Coude tip 106. Formed with a rounded circular tip and a curved body, the Coude tip 106 is conveniently inserted within and easily penetrates through the urethra, thereby aiding in insertion and placement of the stent 100 within the body. A lumen 140 extends through the stent 100 from the fifth section 125 to the first section 105. The lumen terminates within the Coude tip 106. Alternatively, the lumen can extend through the entire stent. The first section 105 is adjacent to a second section 110, which includes an expandable distal malecot 111. The distal malecot 111 has slits 130 between four adjacent movable members 135 of the malecot 111. These slits 130 are in fluid communication with the lumen 140. In alternative embodiments, the distal malecot can have fewer or more movable members. For example, the distal malecot can have two, three, five, six, seven, eight, or more movable members.

The distal malecot 111 is adjacent to a third segment 115, which includes a prostatic segment 116. The prostatic segment 116 is generally tubular with the lumen 140 running therethrough. A spring 158 reinforcing member is positioned within the prostatic segment 116 to provide structural support. The reinforcing member, such as a spring, may take other configurations, such as a coil or individual rings, and may be made of various materials including, but not limited to, plastics and metals, for example, stainless steel, titanium, or nitinol, which provide structural support. In certain embodiments, the spring is made of stainless steel wire. The spring 158 or other type of reinforcing member provides for flexibility along the longitudinal axis of the prostatic segment, while at the same time possessing sufficient radial strength to withstand pressure of the prostatic urethral wall against the prostatic segment 116.

The prostatic segment 116 is adjacent to a fourth section 120, which includes an expandable proximal malecot 121. As shown in FIGS. 1 and 2, the proximal malecot 121 is disposed at about a 45° angle with respect to the prostatic segment 116 and is pointed in a distal direction. Alternatively, the proximal malecot can form an angle of about 0° to about 90° with the prostatic segment. The proximal malecot 121 is formed without slits and defines an enclosed annular structure extending from the stent body. The design of the malecot 121 with an enclosed annular structure extending at an angle from the stent 100 creates a way to anchor the stent 100 within the urethra. The malecot 121 effectively engages the urethral wall as a result of its angled structure, thereby counteracting the tendency of the stent 100 to migrate distally into the bladder. In addition, the angled structure of the malecot 121 prevents high prostatic pressure from collapsing the malecot 121, which may restrict urine flow through the stent 100. Instead, because the malecot 121 is angled over the spring 158, which reinforces the prostatic segment 116, if the prostate presses against the malecot 121, it does not collapse because it is supported by the reinforced prostatic segment 116. Also, the enclosed nature of the proximal malecot 121 smoothes the surface of the malecot 121 that engages the urethra, thereby preventing damage to the urethra, while still allowing the malecot 121 to serve as an effective anchoring structure. Moreover, the enclosed proximal malecot 121 serves to minimize tissue in-growth onto and through the stent 100. Tissue in-growth can impair proper functioning of the stent, including convenient removal of the stent from the urethra.

The proximal malecot 121 is adjacent to a fifth section 125. The fifth section 125 is generally tubular and is located at the proximal end of the stent 100. A retrieval suture 145 is attached to the fifth segment 125. For example, in one embodiment, the suture is attached to the stent by inserting the suture into holes cored into the wall of the stent and subsequently tying a knot such that one suture end proximally extends through the length of urethra. The retrieval suture can be made of various materials including, but not limited to, monofilament suture material. In certain embodiments, the suture is made of 2-0 polybutester.

Figure 13:
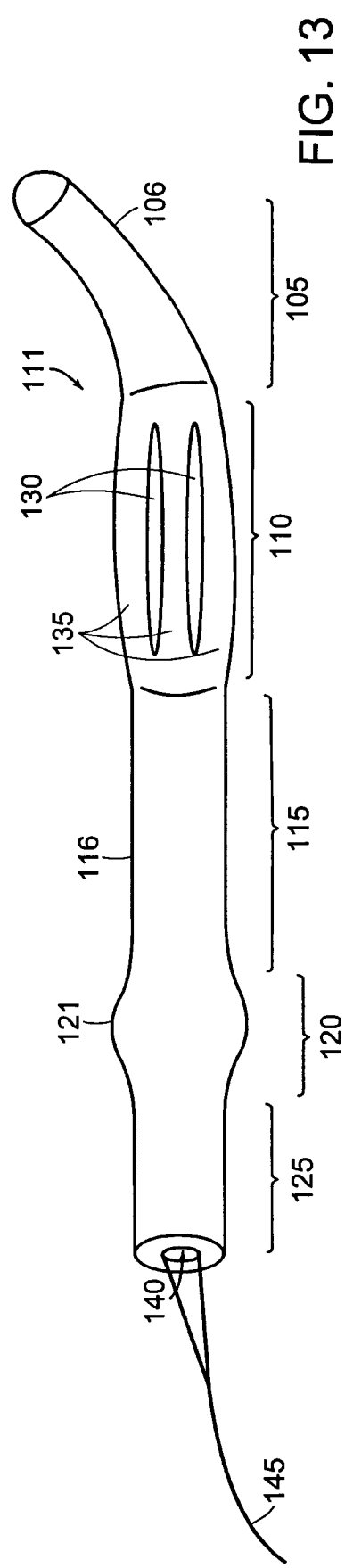
FIG. 13 depicts a schematic rendering of the urethral stent of FIG. 1 in its collapsed, extended form.

Both the distal 111 and proximal malecots 121 of the stent 100 are expandable. Prior to insertion, both malecots 111, 121 are stretched into their collapsed extended positions (as shown in FIG. 13) so as to reduce the size of the stent 100 profile for delivery. As such, the movable members 135 of the distal malecot 111 are substantially flat and close to one another, causing the slits 130 to assume a narrow form. The proximal malecot 121 is also stretched into a collapsed extended position. As such, the proximal malecot 121 is extended and substantially straightened.

Upon insertion, the malecots 111, 121 are released to their relaxed, untensioned positions. As such, the movable members 135 of the distal malecot 111 fold and, thus, are distanced from one another. In turn, the slits 130 widen and enlarge as is shown in FIGS. 1 and 2. Similarly, upon insertion, the proximal malecot 121 assumes its relaxed, untensioned position in which it is angled toward the distal end of the stent 100, as is shown in FIGS. 1 and 2.

When in position within the body, the distal malecot 111 sits within the bladder neck. When in its expanded form (i.e., the movable members 135 are folded so as to widen and enlarge the slits 130), the distal malecot 111 engages the bladder neck wall, thereby preventing anterograde migration of the stent 100 proximally into the urethra. Urine within the bladder enters the stent 100 through these slits 130 and enters the lumen 140 of the stent 100 for eventual release from the body. By comparison, when in position, the proximal malecot 121 engages the prostatic urethral wall, thereby preventing retrograde migration of the stent 100 distally toward the bladder.

The stent can be made of various materials including, but not limited to, elastomeric rubber(s), thermoplastic material(s), or a combination thereof. The elastomeric rubber(s) and thermoplastic material(s) are able to withstand conditions of the inner body environment for the desired period of implantation. Various elastomeric rubber(s) and thermoplastic material(s) possess these characteristics and, thus, are suitable for forming the stent according to the invention. In certain embodiments, the stent is formed of a silicone polymer.

In certain embodiments, the stent is formed of elastomeric rubber(s) or thermoplastic material(s) at lower levels of hardness. As used herein, the terms "hard" and "soft," and various grammatical forms thereof, are general terms meant to generally refer to a difference in properties, including, but not limited to, a relative measure of the durometer value of materials potentially used to form the stent. Use of soft materials can increase patient comfort during implantation of the stent within the body and when the stent is in place within the body. In addition, use of a softer rubber or thermoplastic material can impart the expandable and collapsible properties of the malecots. The ability of the stent to assume a low profile for delivery is a useful feature for insertion and removal of the stent from the body. Stents according to the invention typically are formed of a material having a durometer value of less than about 60 on a Shore A scale. In certain embodiments, the durometer value of the material from which the stent is constructed is less than about 50 on a Shore A scale, about 45 on a Shore A scale, about 40 on a Shore A scale, about 35 on a Shore A scale, about 30 on a Shore A scale, about 25 on a Shore A scale, or about 20 on a Shore A scale. In certain embodiments, the stent is formed of a material having a durometer value of about 30 on a Shore A scale. In other embodiments, different portions of the stent (e.g., the distal malecot, the proximal malecot, and/or the proximal segment) may be formed in a manner such that some or all of these portions are constructed from a material or material(s) having a different durometer value (and, thus, some portions are harder or softer than others). The use of softer, non-rigid materials increases patient comfort and eases insertion and removal of the stent from the body.

The stent, and parts thereof, may be formed by a variety of techniques or a combination of techniques. In certain methods of making the stent according to the invention, the stent is formed by molding the stent as one integral piece. The entire structure of the stent, including the body, the distal malecot with its movable members, the proximal malecot, and the Coude tip, are molded as one integral piece. As such, the stent is molded with the spring contained therein. In some embodiments, the malecots are molded in their expanded form. Molding techniques are used as appropriate to form the stent.

Alternatively, the stent may be formed in parts. For example, the Coude tip, the distal malecot, and the proximal malecot are molded as separate pieces. In some embodiments, the malecots are molded in their expanded form. The prostatic segment is extruded. Subsequently, the two molded malecots, the molded Coude tip, and the extruded prostatic segment are attached as appropriate through the use of adhesives. Various adhesives including, but not limited to, a silicone adhesive of low durometer, such as Room Temperature Vulcanization (RTV) silicone, may be used to attach the pieces of the stent.

The prostatic segment or the entire stent may be molded with the spring in place. Alternatively, the spring can be positioned within the prostatic segment by winding the spring into a radially compressed form and placing it within the prostatic segment. Alternatively, the silicone stent can be initially swollen by immersion in an appropriate solvent, thereby enlarging the openings and the lumen of the stent, followed by placing the spring within the expanded lumen of the prostatic segment. The methods of making the stent as described herein are merely exemplary and are not intended to be the exclusive methods of manufacturing the stent.

Figure 3:
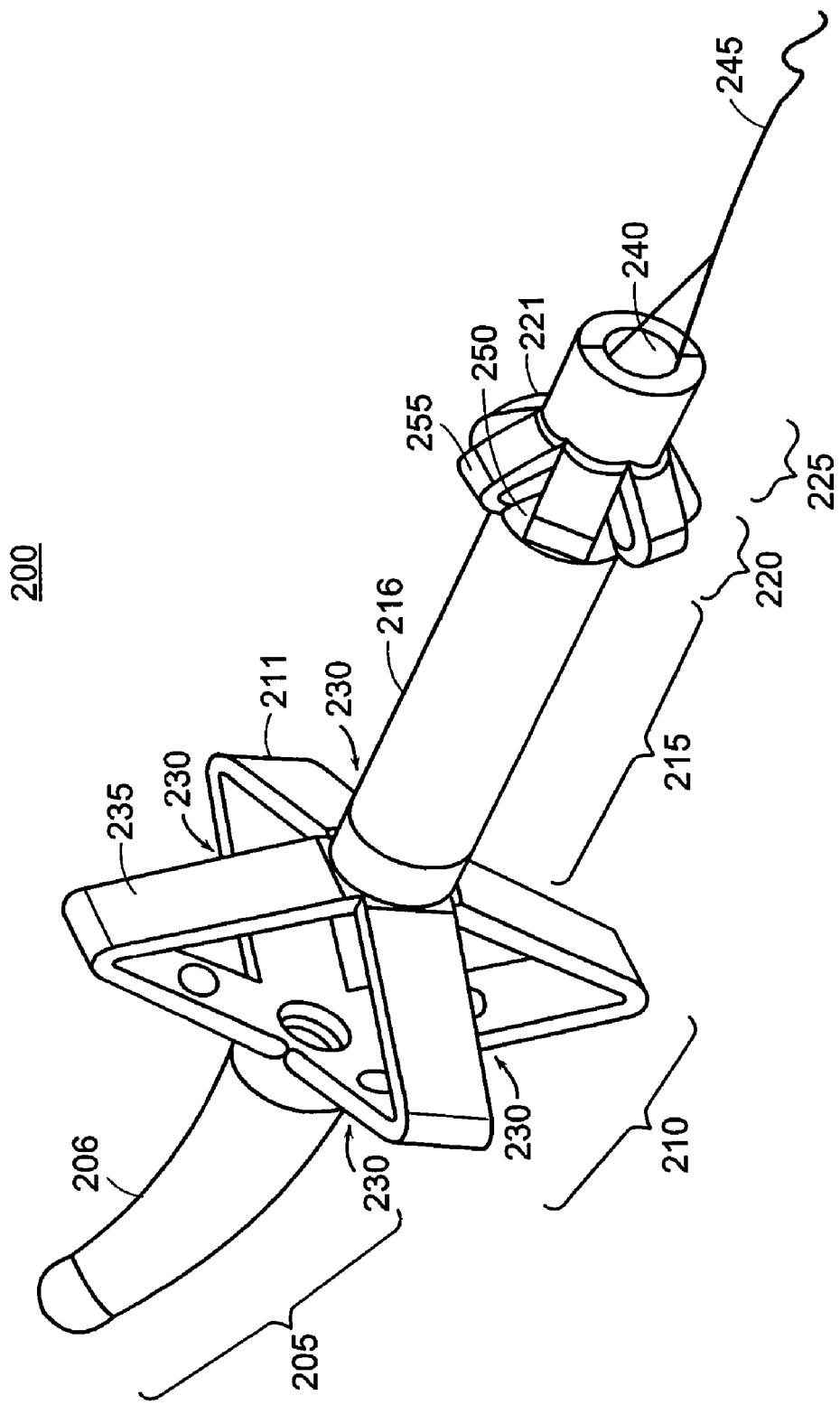
FIG. 3 depicts a schematic rendering of a second embodiment of a urethral stent according to the invention.

In an alternative embodiment, shown in FIG. 3, the stent 200 is designed in a similar manner to the embodiment shown in FIGS. 1 and 2. In this embodiment, the stent 200 has five sections 205, 210, 215, 220, 225. A first section 205, including a Coude tip 206, is adjacent to a second section 210, including a distal malecot 211. The distal malecot 211 possesses slits 230 between movable members 235 of the malecot 211. The second section 210 is adjacent to a third section 215, including a tubular prostatic segment 216. A spring (not shown) is positioned within the prostatic segment 216. The prostatic segment 216 is adjacent to a fourth segment 220, including a proximal malecot 221. By contrast to the embodiment shown in FIGS. 1 and 2, the proximal malecot 221 has slits 250 between six adjacent movable members 255, in a similar manner to the distal malecot 211. In alternative embodiments, the proximal malecot can have fewer or more movable members. For example, the proximal malecot can have two, three, four, five, seven, eight, nine, ten, or more movable members. The slits 250 in this embodiment of the stent 200 are in fluid communication with a lumen 240 extending through at least a portion of the stent 200. The proximal malecot 221 is adjacent to the fifth tubular section 225, which has an attached retrieval suture 245. The lumen 240 extends through the stent 200 from the fifth section 225 to the first section 205. The lumen 240 terminates within the Coude tip 206. Alternatively, the lumen can extend through the entire stent. The malecots 211, 221 of the embodiment shown in FIG. 3 are expandable. The expandable malecots 211, 221 operate in a similar manner as the malecots having slits in the embodiment as shown in FIG. 1, and by a similar mechanism, as will be described in further detail below.

Referring to FIG. 7, an embodiment of an implantation device in association with the stent 100 is shown. An introducer sheath 500 is designed so that its distal end is selectively detachable, via a bushing 510, from the proximal end of the stent 100. The bushing 510 is a tubular structure having an outer diameter of sufficient size to produce an interference fit with the inner diameter of the sheath 500 and the stent 100. The bushing 510 sits securely within the inner diameter of both the distal end of the introducer sheath 500 and the proximal end of the stent 100. The bushing 510 extends farther into the introducer sheath 500 than into the stent 100, thereby creating greater friction and, therefore, a relatively stronger connection between the sheath 500 and the bushing 510 than the stent 100 and the bushing 510. In addition, the inner diameter of the sheath 500 is slightly smaller than the inner diameter of the stent 100, also creating greater friction and therefore, a stronger connection between the sheath 500 and the bushing 510 than between the stent 100 and the bushing 510. This difference in connection strength is useful to facilitate removal of the introducer sheath 500 following implantation of the stent 100, allowing the bushing 510 to remain attached to the introducer sheath 500 and not to the stent 100. Detachment of the sheath 500 and the accompanying bushing 510 from the stent 100 is accomplished by simply pulling on the sheath 500. The bushing may be made of various materials including, but not limited to, polyolefins, nylons, and combinations thereof. The introducer sheath may be made of various materials including, but not limited to, elastomeric rubber(s), thermoplastic material(s), or combinations thereof. In certain embodiments, the introducer sheath is formed of a silicone polymer.

The distal end of a barbed connector 515 is associated with the proximal end of the introducer sheath 500. For example, the distal end of the barbed connector is press fitted into the proximal end of the introducer sheath. FIG. 9 shows a more detailed view of the barbed connector 515, the introducer sheath 500, and the bushing 510.

A stylet 600, whose proximal end is attached to the distal end of a stopcock 620, for example, via an inter-locking mechanism and adhesive, is designed for positioning through the lumens of the barbed connector 515, the introducer sheath 500 and the stent 100. The distal end of the stopcock 620 is selectively detachable to the proximal end of the barbed connector 515 (shown as detached) via an inter-locking mechanism. For example, the distal end of the stopcock 620 has a luer fitting 630 complementary to a luer fitting 530 on the proximal end of the barbed connector 515. The stylet 600 has a balloon 610 near its distal end. In order to control inflation and deflation of the balloon 610, the stylet 600 is attached to the stopcock 620, which includes a valve to prevent or permit inflation or deflation as appropriate. Accordingly, a syringe is attached to the proximal end of the stopcock 620, for example, via a luer fitting 625 on the stopcock 620 and on the syringe (not shown). Upon opening the valve of the stopcock 620, fluid or a gas is injected into the balloon 610, for example, via an inflation lumen running through the stylet 600 and to the balloon 610. An aperture or apertures in the wall of the stylet 600 allows communication between the inflation lumen and the balloon 610. Similarly, fluid is removed from the balloon 610, for example, via the inflation lumen running through the stylet 600, using a syringe. The stylet may be made of various materials including, but not limited to, polyolefins, nylons, or combinations thereof. The stylet 600 is sufficiently rigid to apply pressure against the Coude tip 106 and to stretch the stent 100 into its collapsed extended form, as described in more detail below. FIG. 10 shows a more detailed view of the stylet 600, the associated balloon 610, and the stopcock 620.

The balloon may be made from a variety of materials. In certain embodiments, the balloon is formed of a silicone polymer. For example, the balloon is a silicone tube that is slid over the distal end of the stylet, to a position about 0.5 inches from the distal end of the stylet. The ends of the silicone tube are adhered to and tied by sutures to the stylet. In addition, adhesive, for example, epoxy adhesive, is layered over the sutures to secure the ends of the silicone tube to the stylet and to smooth the transition between the stylet body and the balloon portion. Alternatively, the balloon can be formed through a blow molding process. Briefly, in the blow molding process, a section of tubing is expanded about its middle section, leaving the ends (i.e., the bands) unexpanded. The bands are bonded to the stylet. Bonding can be accomplished through the use of an adhesive bond, through the use of a shrink fit bond, through the use of an RF bond, through the use of an ultrasonic bond, or through the use of a laser bond.

Figure 14:
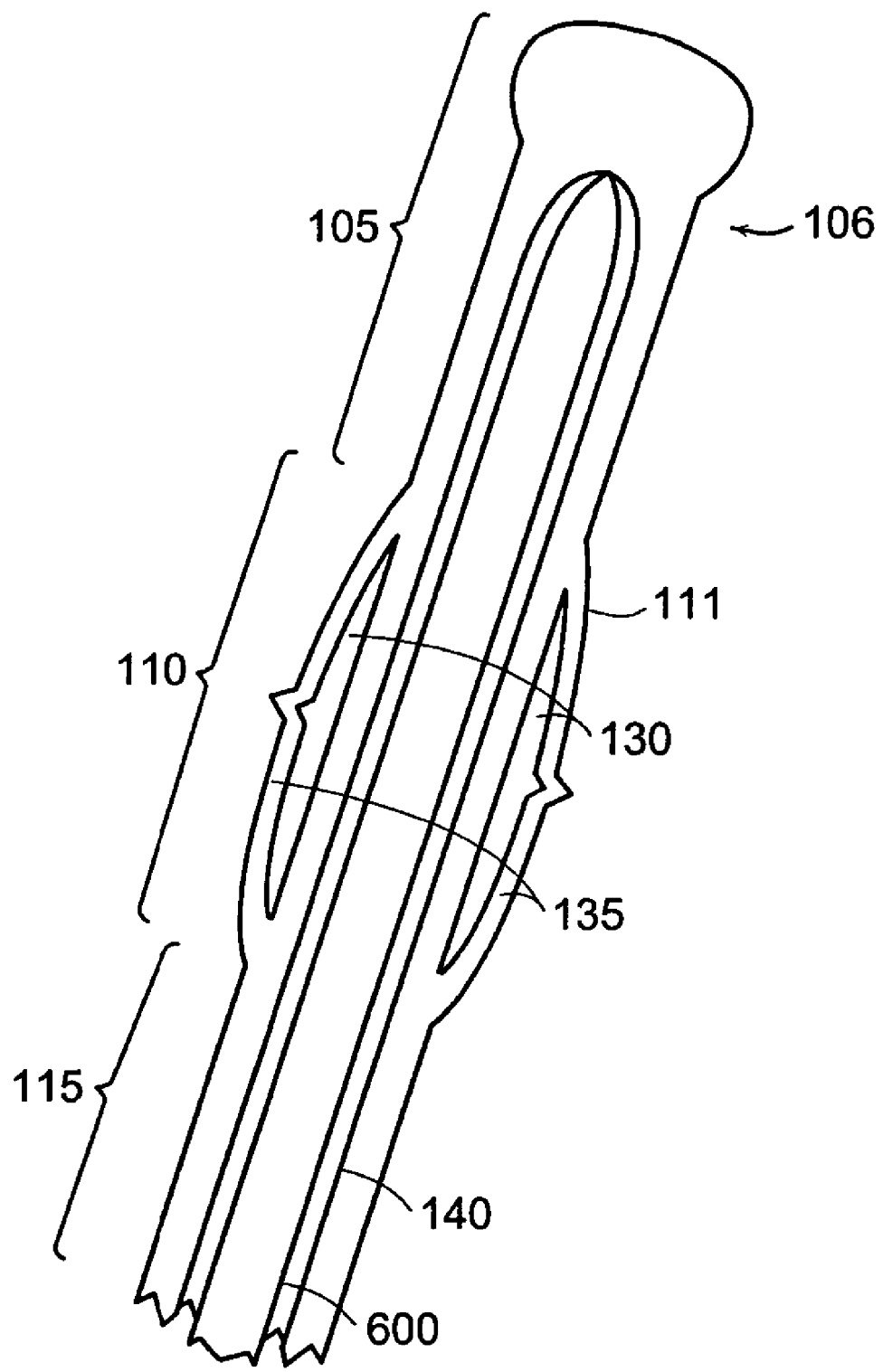
FIG. 14 depicts a schematic rendering of a portion of the urethral stent of FIG. 1 and an associated implantation device.

Various methods can be used to insert the stent according to the invention within the body. In one exemplary embodiment of a method for inserting a stent 100 according to the invention, the stent 100 is tensioned such that the malecots 111, 121 are in their collapsed extended position prior to insertion of the stent 100 within the body. The proximal end of the stent 100 is connected via the bushing 510 to the distal end of the insertion sheath 500. The proximal end of the insertion sheath 500, in turn, is press fitted to the distal end of the barbed connector 515 so that the stent 100, the sheath 500 and the barbed connector 515 are attached linearly. The retrieval suture 145 extends from the proximal end of the stent 100 through the lumen of the sheath 500 and the barbed connector 515. The suture 145 is tensioned and pulled back against the barbed connector 515. The stylet 600, attached to the distal end of the stopcock 620, is inserted through the barbed connector 515, the insertion sheath 500, and the stent 100. The distal end of the stylet 600 abuts and pushes against the end of the lumen 140 inside of the Coude tip 106 of the stent 100 (FIG. 14), causing the stent 100 and the malecots 111, 121 to stretch into their collapsed, extended positions as described earlier and as shown in FIG. 13. Once the stent 100 is stretched into its collapsed form, the luer fittings 530, 630 between the barbed connector 515 and the stopcock 620 are locked such that the retrieval suture 145 is locked in its taut form between the luer fittings 530, 630. The syringe is connected to the stylet 600 via the luer fitting 625 at the proximal end of the stopcock 620. Air from the balloon 610, attached to the stylet 600, is purged. For example, about four cc of sterile water or saline is infused into the balloon 610 with a five cc syringe. The balloon 610 is deflated followed by closing the stopcock 620 and removing the syringe from the stylet 600. Prior to insertion of the stent 100, the stent 100 should be lubricated with a sterile liquid or gel lubricant.

The patient also is prepared prior to insertion of the stent 100 within the urethra 715. The patient's bladder 700 should contain at least about 150 cc of fluid prior to stent 100 insertion. Also, about twenty cc of an anesthetic lubricant is injected into the urethra 715 followed by occlusion or clamping of the penile meatus for about five to ten minutes to prevent lubricant leakage prior to stent 100 placement.

Figure 15:
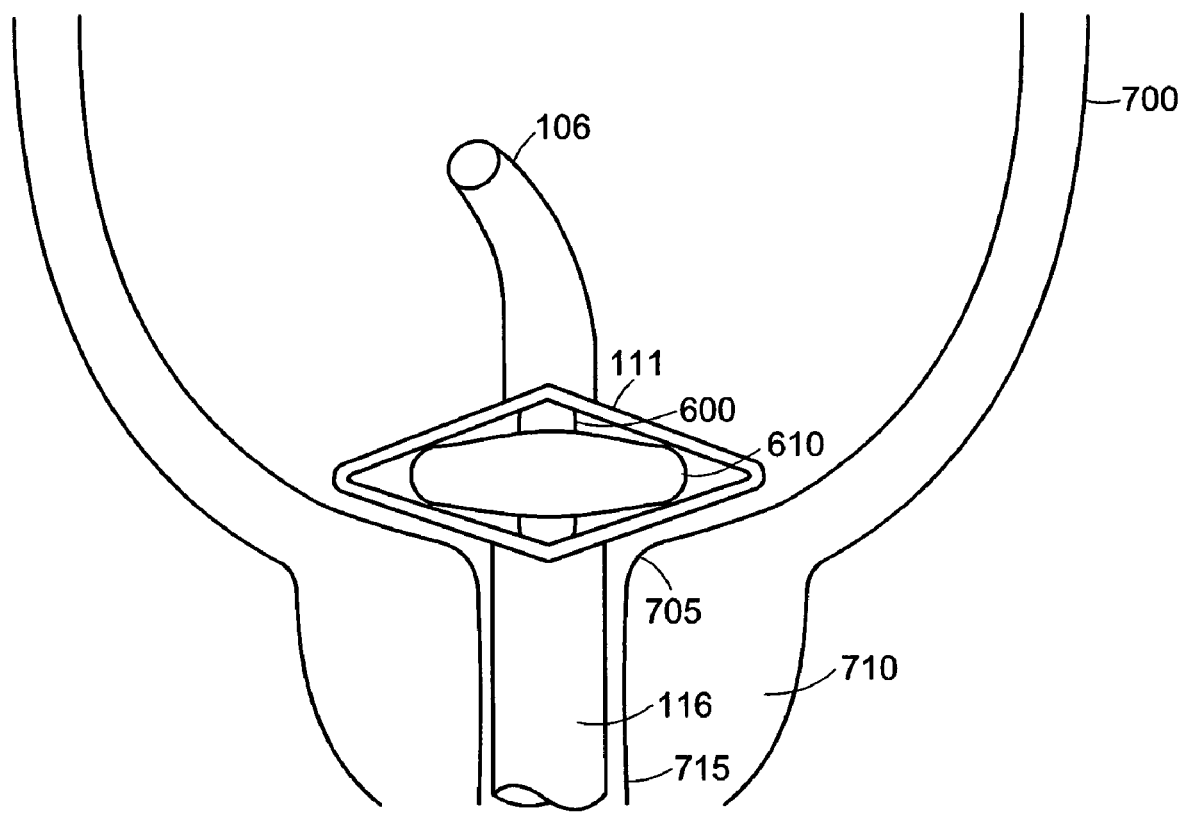
FIG. 15 depicts a schematic rendering of a portion of the urethral stent of FIG. 1 and an associated implantation device, as placed within the body.

Upon preparation of the patient and the stent 100, the tensioned stent 100 and the associated implantation device are inserted into the urethral meatus. To allow easy passage through the sphincter, the Coude tip 106 is pointed anteriorly while the patient is in a supine position. The stent 100 is advanced slowly and transurethrally until the Coude tip 106 passes through the striated sphincter 720 and contacts the bladder 700 wall. The flow of urine from the proximal end of the delivery system serves as confirmation that the Coude tip 106 has properly contacted the bladder 700 wall. Then, the luer fittings 630, 530 between the stopcock 620 and the barbed connector 515 are unlocked in order to release the tension on the retrieval suture 145 and to remove the force of the distal end of the stylet 600 against the Coude tip 106. The malecots 111, 121, thus, assume their relaxed form. The material forming the stent 100 possesses an inherent shape memory property by which the material, once set, for example, by curing, may be compelled to stretch into an unnatural position by the exertion of an external force. However, upon removal of the external force, the material will reassume its relaxed position. As such, the release of tension on the retrieval suture 145 and the removal of the stylet 600 pressure on the Coude tip 106, allows the proximal malecot 121 to assume its relaxed position in which it is angled toward the distal end of the stent 100. Moreover, the movable members 135 of the distal malecot 111 naturally fold and extend outward so as to cause the slits 130 to widen and expand. The syringe, filled with sterile water or saline, is reattached to the stopcock 620. The stopcock 620 is opened and the balloon 610 is inflated with about four cc of fluid from the syringe. In part, inflation of the balloon 610 can serve to aid in the expansion of the distal malecot 111 into its anchoring form. After inflation of the balloon 610, the syringe, retrieval suture 145, and stylet 600 are simultaneously pulled back proximally so that the distal bladder malecot 111 contacts the bladder neck 705. At this point, the distal bladder malecot 111 and the expanded balloon are seated in the bladder neck 705, and the prostatic segment 116 is positioned within the urethra 715 surrounded by the prostate 710 (FIG. 15). The balloon 610 provides the structure that resists the entire stent 100 from being pulled out of the bladder 700 during the seating procedure but which provides the manner in which the distal bladder malecot 111 is seated. Accordingly, the stent 100 is properly positioned without having to perform additional procedures to ensure proper stent placement. After deflation of the balloon 610, the syringe and the stylet 600 are slowly retracted. The insertion sheath 500 is held during this process so as to maintain the stent 100 position. The insertion sheath 500 then is carefully retracted so as to detach the bushing 510 from the proximal end of the stent 100. The retrieval suture 145 is cut at the penile meatus or inside the meatus. The patient's ability to control voiding confirms satisfactory functioning of the striated sphincter 720.

As shown in FIG. 11, upon insertion of the stent 100 and the associated implantation device, and prior to removal of the stylet 600 and the insertion sheath 500, the expanded distal malecot 111 is seated within the bladder neck 705 of the bladder 700 so as to prevent proximal migration of the stent 100. The prostatic segment 116 is positioned within the prostatic urethra 715 so as to maintain the patency of the prostatic urethra 715 against collapsing prostate 710 pressure. The spring (not shown) within the prostatic segment 115 provides structural support. The proximal malecot 120 is positioned within the prostatic urethra 715 in its angled expanded form so as to prevent distal migration of the stent 100 into the bladder 700. The fifth section 125 is positioned distal of the external striated sphincter 720 so as not to impair proper functioning of the sphincter 720 in controlling urine discharge.

In order to remove the stent 100 from the urethra, the urethra is filled with local anesthetic gel. The retrieval suture 145 is gently but firmly pulled until the stent 100 is removed.

Figure 4:
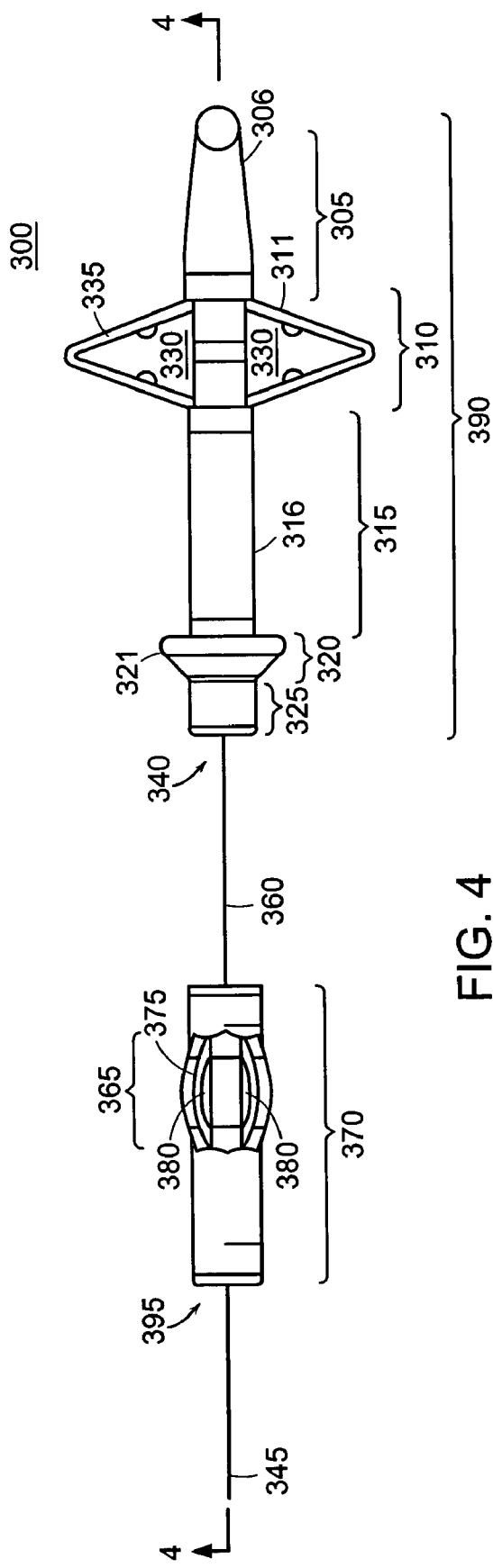
FIG. 4 depicts a schematic rendering of a third embodiment of a urethral stent according to the invention.
Figure 5:
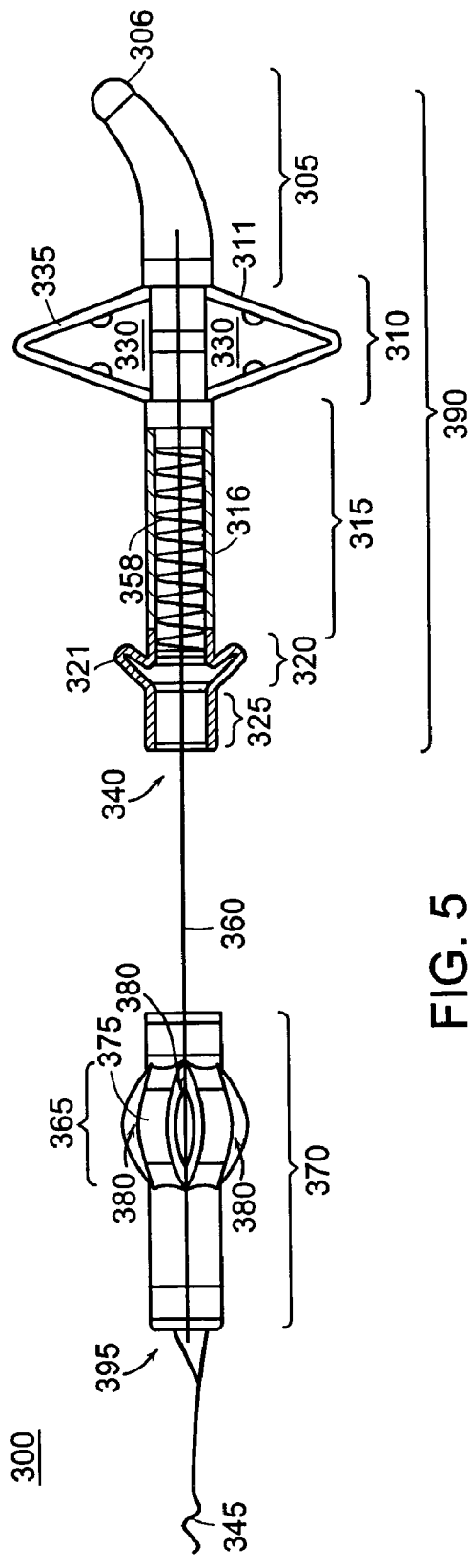
FIG. 5 depicts a schematic rendering of a cross section of the embodiment of the urethral stent of FIG. 4 taken along section line 4-4.

Referring to FIGS. 4 and 5, an alternative embodiment of the stent 300, a bulbar design, according to the invention is shown. Generally, the stent has a primary stent body 390 attached to a bulbous urethral segment 370. The primary stent body 390 has five sections 305, 310, 315, 320, 325. A first section 305, including a Coude tip 306, is located at the distal end of the primary stent body 390 and aids in insertion of the stent 300 within the body. Formed with a rounded circular tip and a curved body, the Coude tip 306 is conveniently inserted within and easily penetrates through the urethra, thereby aiding in insertion and placement of the stent 300 within the body. A lumen 340 extends through the stent 300 from the fifth section 325 to the first section 305. The lumen 340 terminates within the Coude tip 306. Alternatively, the lumen can extend through the entire stent. The first section 305 is adjacent to a second section 310, which includes an expandable distal malecot 311. The distal malecot 310 has slits 330 between four adjacent movable members 335 of the malecot 310. These slits 330 are in fluid communication with the lumen 340. In alternative embodiments, the distal malecot can have fewer or more movable members. For example, the distal malecot can have two, three, five, six, seven, eight, or more movable members.

The distal malecot 320, in turn, is adjacent to a third segment 315, which includes a prostatic segment 316. The prostatic segment 316 is generally tubular with the lumen 340 running therethrough. A spring 358 reinforcing member is positioned within the prostatic segment 316 to provide structural support. The reinforcing member, such as a spring, may take other configurations, such as a coil or individual rings, and may be made of various materials including, but not limited to, plastics and metals, for example, stainless steel, titanium, and nitinol, which provide structural support. In certain embodiments, the spring is made of stainless steel wire. The spring 358 or other type of reinforcing member provides for flexibility along the longitudinal axis of the prostatic segment, while at the same time possessing sufficient radial strength to withstand pressure of the prostatic urethral wall against the prostatic segment 316.

The prostatic segment 316 is adjacent to a fourth section 320, which includes an expandable proximal malecot 321. As shown in FIGS. 4 and 5, the proximal malecot 321 is disposed at about a 45° angle with respect to the prostatic segment 316 and is pointed in a distal direction. Alternatively, the proximal malecot can form an angle of about 0° to about 90° with the prostatic segment. The proximal malecot 321 is formed without slits and defines an enclosed annular structure extending from the stent body. The design of the malecot 321 with an enclosed annular structure extending at an angle from the stent 300 creates a way by which to anchor the stent 300 within the urethra. The malecot 321 effectively engages the urethral wall as a result of its angled structure, thereby counteracting the tendency of the stent 300 to migrate distally into the bladder. In addition, the angled structure of the malecot 321 prevents high prostatic pressure from collapsing the malecot 321 which may restrict urine flow through the stent 300. Instead, because the malecot 321 is angled over the spring 358, which reinforces the prostatic segment 316, if the prostate presses against the malecot 321, it does not collapse because it is supported by the reinforced prostatic segment 316. Also, the enclosed nature of the proximal malecot 321 smoothes the surface of the malecot 321 that engages the urethra, thereby preventing damage to the urethra, while still allowing the malecot 321 to serve as an effective anchoring structure. Moreover, the enclosed proximal malecot 321 serves to minimize tissue in-growth onto and through the stent 300. Tissue in-growth can impair proper functioning of the stent, including convenient removal of the stent from the urethra.

The proximal malecot 321 is adjacent to a fifth section 325. The fifth section 325 is generally tubular and is located at the proximal end of the primary stent body 390.

By comparison to the non-bulbar design embodiments described earlier, the bulbar design embodiment 300 according to the invention has a bulbous urethral segment 370 attached to the primary stent body 390. The bulbous urethral segment 370 is attached to the primary stent body 390 by at least one connector suture 360. The connector suture 360 is attached at the proximal end of the primary stent body 390 and at the distal end of the bulbous urethral segment 370. For example, the connector suture is inserted into holes cored through the walls of the proximal end of the primary stent body and of the distal end of the bulbous urethral segment, respectively. The connector can take a form other than a suture, so long as the connector provides for normal functioning of the urethral sphincter while the stent is in place. The bulbous urethral segment 370 is a generally tubular body with a lumen 395 running therethrough. The bulbous urethral segment 370 has an optional bulbar malecot 365. The bulbar malecot 365 is formed so as to possess slits 380 between adjacent movable members 375 of the malecot 365. The bulbar malecot functions, in part, to provide additional resistance against migration of the stent in the distal direction toward the bladder.

A retrieval suture 345 is attached to the bulbous urethral segment 370. For example, in one embodiment, the retrieval suture is attached to the stent by inserting the suture into holes cored into a wall of the bulbous urethral segment. The retrieval suture and the connector suture can be made of various materials including, but not limited to, monofilament suture material. In certain embodiments, the sutures are made of 2-0 polybutester.

Each of the distal 311, proximal 321, and bulbar 365 malecots are expandable. Prior to insertion, the malecots 311, 321, 365 are stretched into their collapsed extended positions (in a similar manner to the first embodiment as shown in FIG. 13), so as to reduce the size of the stent 300 profile for delivery. As such, the movable members 335, 375 of the distal 311 and bulbar 365 malecots are substantially flat and close to one another, causing the slits 330, 380 to assume narrow forms. The proximal malecot 321 is also stretched into a collapsed, extended position. As such, the proximal malecot 321 is extended and substantially straightened.

Upon insertion, the malecots 311, 321, 365 are released to their relaxed, untensioned positions. As such, the movable members 335 of the distal malecot 311 fold and, thus, are distanced from one another. Similarly, the movable members 375 of the bulbar malecot 365 bulge outward and, thus, are also distanced from one another. In turn, the slits 330, 380 widen and enlarge as shown in FIGS. 4 and 5. Similarly, upon insertion, the proximal malecot 321 assumes its relaxed, untensioned position in which it is angled toward the distal end of the stent 300 as shown in FIGS. 4 and 5.

When in position within the body, the distal malecot 311 sits within the bladder neck. When in its expanded form (i.e., the movable members 335 are folded so as to widen and enlarge the slits 330), the distal malecot 311 engages the bladder neck wall, thereby preventing anterograde migration of the stent 300 proximally into the urethra. Urine within the bladder enters the stent through these slits 330 and enters the lumen 340 of the stent 300 for eventual release from the body. By comparison, when in position, the proximal malecot 321 engages the prostatic urethral wall, thereby preventing retrograde migration of the stent 300 distally toward the bladder. The bulbar malecot 365, when in position, engages the urethral wall and provides additional resistance against both distal migration of the stent toward the bladder and proximal migration of the stent away from the bladder. When the stent is properly positioned, the connector sutures span the urethral sphincter, thereby able for proper functioning of the sphincter while the stent is in place. The sphincter is allowed to constrict and expand around the connector sutures so as to properly control urine flow.

The stent can be made of various materials including, but not limited to, elastomeric rubber(s), thermoplastic material(s), or a combination thereof. The elastomeric rubber(s) and thermoplastic material(s) are able to withstand conditions of the inner body environment for the desired period of implantation. Various elastomeric rubber(s) or thermoplastic material(s) possess this characteristic and, thus, are suitable for forming the stent according to the invention. In certain embodiments, the stent is formed of a silicone polymer.

In certain embodiments, the stent is formed of elastomeric rubber(s) or thermoplastic material(s) at lower levels of hardness. As used herein, the terms "hard" and "soft," and various grammatical forms thereof, are general terms meant to generally refer to a difference in properties, including, but not limited to, a relative measure of the durometer value of materials potentially used to form the stent. Use of soft materials can increase patient comfort during implantation of the stent within the body and when the stent is in place within the body. In addition, use of a softer rubber or thermoplastic material can impart the expandable and collapsible properties of the malecots. The ability of the stent to assume a low profile for delivery is a useful feature for insertion and removal of the stent from the body. Stents according to the invention typically are formed of a material having a durometer value of less than about 60 on a Shore A scale. In certain embodiments, the durometer value of the material from which the stent is constructed is less than about 50 on a Shore A scale, about 45 on a Shore A scale, about 40 on a Shore A scale, about 35 on a Shore A scale, about 30 on a Shore A scale, about 25 on a Shore A scale, or about 20 on a Shore A scale. In certain embodiments, the stent is formed of a material having a durometer value of about 30 on a Shore A scale. In other embodiments, different portions of the stent (e.g., the distal malecot, the proximal malecot, the bulbar malecot, and/or the proximal segment) may be formed in a manner such that some or all of these portions are constructed from a material or material(s) having a different durometer value (and, thus, some portions are harder or softer than others). The use of softer, non-rigid materials increases patient comfort and eases insertion and removal of the stent from the body.

The stent, and parts thereof, may be formed by a variety of techniques or a combination of techniques. In certain methods of making the stent according to the invention, the stent is formed by molding each of the primary stent body and the bulbous urethral segments as one integral piece. The entire structure of the primary stent body, including the prostatic segment, the distal malecot with its movable members, the proximal malecot and the Coude tip, are molded as one integral piece. As such, the primary stent body is molded with the spring contained therein. In addition, the bulbous urethral segment is molded as one integral piece. In some embodiments, the malecots are molded in their expanded position. Molding techniques may be used as appropriate to form the stent. The bulbous urethral segment and the primary stent body are connected by inserting the at least one connector suture into holes cored into walls of the primary stent body and the bulbous urethral segment, respectively.

Alternatively, the stent may be formed in parts. For example, the Coude tip, the distal malecot, the proximal malecot and the bulbous urethral segment are molded as separate pieces. In some embodiments, the malecots are molded in their expanded position. The prostatic segment is extruded. Subsequently, the two molded malecots, the molded Coude tip, and the extruded prostatic segment are attached as appropriate through the use of adhesives. Various adhesives including, a silicone adhesive of low durometer, such as Room Temperature Vulcanization (RTV) silicone may be used to attach the pieces of the stent. Subsequently, the bulbous urethral segment and the primary stent body are attached via the at least one connector suture as described above.

The prostatic segment or the primary stent body may be molded with the spring in place. Alternatively, the spring can be positioned within the prostatic segment by winding the spring into a radially compressed form and placing it within the prostatic segment. Alternatively, the silicone primary stent body can be initially swollen by immersion in an appropriate solvent, thereby enlarging the openings and the lumen of the primary stent body, followed by placing the spring within the expanded lumen of the prostatic segment.

As described earlier, the retrieval suture 345 is attached to the proximal end of the bulbous urethral segment 370. The methods of making the stent as described herein are merely exemplary and are not intended to be the exclusive methods of manufacturing the stent.

In an alternative embodiment as shown in FIG. 6, the stent 400 is designed in a similar manner to the embodiment shown in FIGS. 4 and 5. In this embodiment, the stent 400 has a primary stent body 490 having five sections 405, 410, 415, 420, 425. A first section 405, including a Coude tip 406, is adjacent to a second section 410, including a distal malecot 411. The distal malecot 411 possesses slits 430 between movable members 435 of the malecot 410. The second section 410 is adjacent to a third section 415, including a tubular prostatic segment 416. A spring (not shown) is positioned within the prostatic segment 416. The prostatic segment 416 is adjacent to a fourth segment 420, including a proximal malecot 421. By contrast to the embodiment shown in FIGS. 4 and 5, the proximal malecot 421 has slits 450 between six adjacent movable members 455, in a similar manner as the distal malecot 411. In alternative embodiments, the proximal malecot can have fewer or more movable members. For example, the proximal malecot can have two, three, four, five, seven, eight, nine, ten, or more movable members. The slits 450 in this embodiment of the stent 400 are in fluid communication with a lumen 440 extending through at least a portion of the primary stent body 490. The proximal malecot 421 is adjacent to a fifth tubular section 425. The lumen 440 extends through the stent 400 from the fifth section 425 to the first section 405. The lumen 440 terminates within the Coude tip 406. Alternatively, the lumen can extend through the entire stent. The fifth tubular section 425 is attached to a bulbous urethral segment 470 by at least one connecting suture 460. The bulbous urethral segment 470, defining a lumen 495, has a bulbar malecot 465 having slits 480 between adjacent members 475. A retrieval suture 445 is attached near or at the proximal end of the bulbous urethral segment 470. The malecots 411, 421, 465 of the embodiment shown in FIG. 6 are expandable. The expandable malecots 411, 421, 465 operate in a similar manner as the malecots having slits in the third embodiment as shown in FIGS. 4 and 5, and by a similar mechanism, as will be described in further detail below.

Referring to FIG. 8, an embodiment of an implantation device in association with the stent 300 is shown. An introducer sheath 500 is designed so that its distal end is selectively detachable, via a bushing 510, from the proximal end of the bulbous urethral segment 370. The bushing 510 is a tubular structure having an outer diameter of sufficient size to produce an interference fit with the inner diameter of the sheath 500 and the bulbous urethral segment 370. The bushing 510 sits securely within the inner diameter of both the distal end of the introducer sheath 500 and the proximal end of the bulbous urethral segment 370. The bushing 510 extends farther into the introducer sheath 500 than into the bulbous urethral segment 370, thereby creating greater friction and, therefore, a relatively stronger connection between the sheath 500 and the bushing 510 than the stent 300 and the bushing 510. In addition, the inner diameter of the sheath 500 is slightly smaller than the inner diameter of the bulbous urethral segment 370, also creating greater friction and therefore, a stronger connection between the sheath 500 and the bushing 510 than between the stent 300 and the bushing 510. This difference in connection strength is useful to facilitate removal of the introducer sheath 500 following implantation of the stent 300, allowing the bushing 510 to remain attached to the introducer sheath 500 and not to the stent 300. Detachment of the sheath 500 and the accompanying bushing 510 from the stent 300 is accomplished by simply pulling on the sheath 500. The bushing may be made of various materials including, but not limited to, polyolefins, nylons, and combinations thereof. The introducer sheath may be made of various materials including, but not limited to, elastomeric rubber(s), thermoplastic material(s), or combinations thereof. In certain embodiments, the introducer sheath is formed of a silicone polymer.

The distal end of a barbed connector 515 is associated with the proximal end of the introducer sheath 500. For example, the distal end of the barbed connector is press fitted into the proximal end of the introducer sheath. FIG. 9 shows a more detailed view of the barbed connector 515, the introducer sheath 500, and the bushing 510.

A stylet 600, whose proximal end is attached to the distal end of a stopcock 620, for example, via an inter-locking mechanism and adhesive, is introduced through the length of the barbed connector 515, the introducer sheath 500 and the entire stent 300. The distal end of the stopcock 620 is selectively detachable to the proximal end of the barbed connector 515 (shown as detached) via an inter-locking mechanism. For example, the distal end of the stopcock has a luer fitting 630 complementary to a luer fitting 530 on the proximal end of the barbed connector 515. The stylet 600 has a balloon 610 near its distal end. In order to control inflation and deflation of the balloon 610, the stylet 600 is attached to the stopcock stent 620, which includes a valve to prevent or permit inflation or deflation as appropriate. Accordingly, a syringe is attached to the proximal end of the stopcock 620, for example, via a luer fitting 625 on the stopcock 620 and on the syringe (not shown). Upon opening the valve of the stopcock 620, fluid or a gas is injected into the balloon 610, for example, via an inflation lumen running through the stylet 600 and to the balloon 610. An aperture or apertures in the wall of the stylet 600 allows communication between the inflation lumen and the balloon 610. Similarly, fluid is removed from the balloon 610, for example, via the inflation lumen running through the stylet 600, using a syringe. The stylet may be made of various materials including, but not limited to, polyolefins, nylons, or combinations thereof. The stylet 600 is sufficiently rigid to apply pressure against the Coude tip 306 and to stretch the device 300 into its collapsed form, as described in more detail below. FIG. 10 shows a more detailed view of the stylet 600, the associated balloon 610, and the stopcock 620.

The balloon may be made from a variety of materials. In certain embodiments, the balloon is formed of a silicone polymer. For example, the balloon is a silicone tube that is slid over the distal end of the stylet to a position, about 0.5 inches from the distal end of the stylet. The ends of the silicone tube are adhered to and tied by sutures to the stylet. In addition, adhesive, for example, epoxy adhesive, is layered over the sutures to secure the ends of the silicone tube to the stylet and to smooth the transition between the stylet body and the balloon portion. Alternatively, the balloon can be formed through a blow molding process. Briefly, in the blow molding process, a section of tubing is expanded about its middle section, leaving the ends (i.e., the bands) unexpanded. The bands are bonded to the stylet. Bonding can be accomplished through the use of an adhesive bond, through the use of a shrink fit bond, through the use of an RF bond, through the use of an ultrasonic bond, or through the use of a laser bond.

Various methods can be used to insert the stent according to the invention within the body. In one exemplary embodiment of a method for inserting a stent 300 according to the invention, the stent 300 is tensioned such that the malecots 311, 321, 365 are in their collapsed extended position prior to insertion of the stent 300 within the body. The proximal end of the bulbous urethral segment 370 of the stent 300 is connected via the bushing 510 to the distal end of the insertion sheath 500. The proximal end of the insertion sheath 500, in turn, is press fitted to the distal end of the barbed connector 515 so that the stent 300, the sheath 500 and the barbed connector 515 are attached linearly. The retrieval suture 345 extends through the lumen of the sheath 500 and the barbed connector 515. The suture 345 is tensioned and pulled back against the barbed connector 515. The stylet 600, attached to the distal end of the stopcock 620 is inserted through the barbed connector 515, the insertion sheath 500, and the entire stent 300, including both the bulbous urethral segment 370 and the primary stent body 390. The distal end of the stylet 600 abuts and pushes against the end of the lumen 340 inside of the Coude tip 306 of the stent 300 (as shown for the non-bulbar embodiment in FIG. 14) causing the stent 300 and the malecots 311, 321, 365 to stretch into their collapsed extended positions, as described earlier. Once the stent 300 is stretched into its collapsed form, the luer fittings 530, 630 between the barbed connector 515 and the stopcock 620 are locked, such that the retrieval suture is locked in its taut form between the luer fittings 530, 630. The syringe is connected to the stylet 600 via a luer fitting 625 at the proximal end of the stopcock 620. Air from the balloon 610, attached to the stylet 600, is purged. For example, about four cc of sterile water or saline is infused into the balloon 610 with a five cc syringe. The balloon is deflated followed by closing the stopcock 620 and removing the syringe from the stylet 600. Prior to insertion of the stent 300, the stent 300 should be lubricated with a sterile liquid or gel lubricant.

The patient also is prepared prior to insertion of the stent 300 within the urethra. The patient's bladder 700 should contain at least about 150 cc of fluid prior to stent 300 insertion. Also, about twenty cc of an anesthetic lubricant is injected into the urethra 715 followed by occlusion or clamping of the penile meatus for about five to ten minutes to prevent lubricant leakage prior to stent 300 placement.

Upon preparation of the patient and the stent 300, the tensioned stent 300 and associated implantation device are inserted into the urethral meatus. To allow easy passage through the sphincter, the Coude tip 306 is pointed anteriorly while the patient is in a supine position. The stent 300 is advanced slowly and transurethrally until the Coude tip 306 passes through the striated sphincter 720 and contacts the bladder 700 wall. The flow of urine from the proximal end of the delivery system serves as confirmation that the Coude tip 306 has properly contacted the bladder 700 wall. Then, the luer fittings 630, 530 between the stopcock 620 and the barbed connector 515 are unlocked in order to release the tension on the retrieval suture 345 and to remove the force of the distal end of the stylet 600 against the Coude tip 306. The malecots 311, 321, 365, thus assume their relaxed form. The material forming the stent 300 possesses an inherent shape memory property by which the material, once set, for example, by curing, may be compelled to stretch into an unnatural position by the exertion of an external force. However, upon removal of the external force, the material will reassume its relaxed position. As such, the release of tension on the retrieval suture 345 and the removal of the stylet 600 pressure on the Coude tip 306, allows the proximal malecot 321 to assume its relaxed position in which it is angled toward the distal end of the stent 300. Moreover, the movable members 335 of the distal malecot 311 naturally fold and extend outward so as to cause the slits 330 to widen and expand. Similarly, the movable members 375 of the bulbar malecot 365 naturally bulge outward so as to cause the slits 380 to widen and expand. The syringe, filled with sterile water or saline, is reattached to the stopcock 620 at the luer fitting 625. The stopcock 620 is opened and the balloon is inflated with about four cc of fluid from the syringe. In part, inflation of the balloon 610 can serve to aid in the expansion of the distal malecot 311 into its anchoring form. After inflation of the balloon 610, the syringe, retrieval suture 345, and stylet 600 are simultaneously pulled back proximally so that the distal bladder malecot 311 contacts the bladder neck 705. At this point, the distal bladder malecot 311 and the expanded balloon are seated in the bladder neck 705, and the prostatic segment 316 is positioned within the urethra 715 surrounded by the prostate 710 (as shown for the first embodiment in FIG. 15). The bulbous urethral segment 370 is seated in the urethra 715 proximal to the external striated sphincter 720. The balloon 610 provides the structure that resists the entire stent 300 from being pulled out of the bladder 700 during the seating procedure but which provides the manner in which the distal bladder malecot is seated. Accordingly, the stent 300 is positioned without having to perform additional procedures to ensure proper stent placement. After deflation of the balloon 610, the syringe and the stylet 600 are slowly retracted. The introduction sheath 500 is held during this process so as to maintain the stent 300 position. The insertion sheath 500 then is carefully retracted so as to detach the bushing 510 from the proximal end of the bulbous urethral segment 370. The retrieval suture 345 is cut at the penile meatus or inside the meatus. The patient's ability to control voiding confirms satisfactory functioning of the striated sphincter 720.

Figure 12:
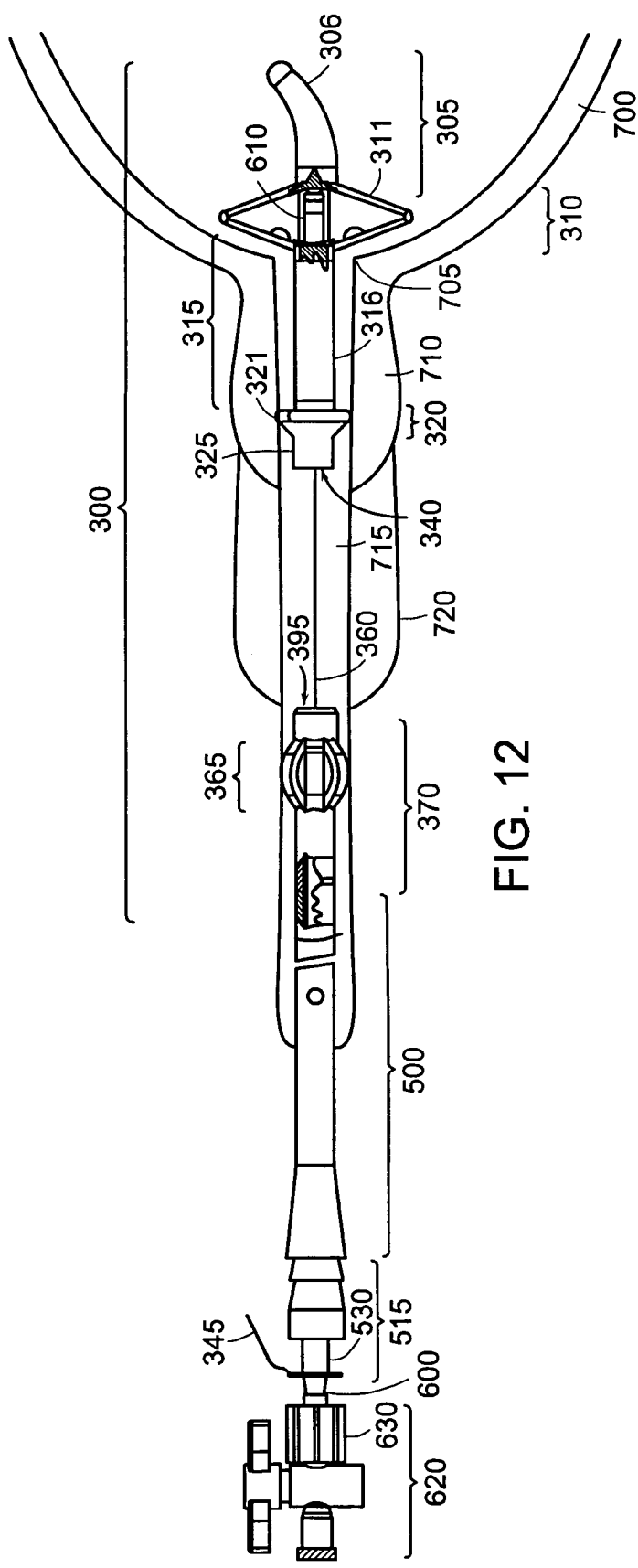
FIG. 12 depicts a schematic rendering of the urethral stent of FIG. 4 associated with the implantation device of FIG. 8, as placed within the body.

As shown in FIG. 12, upon insertion of the stent 300 and the associated implantation device and prior to removal of the insertion sheath 500 and the stylet 600, the expanded distal malecot 310 is seated within the bladder neck 705 of the bladder 700 so as to prevent proximal migration of the stent 300. The prostatic segment 315 is positioned within the prostatic urethra 715 so as to maintain the patency of the prostatic urethra 715 against collapsing prostate 710 pressure. The spring (not shown) within the prostatic segment 315 provides additional structural support. The proximal malecot 320 is positioned within the prostatic urethra 710 in its angled expanded form so as to prevent distal migration of the stent 300 into the bladder 700. The fifth section 325 is positioned distal of the external striated sphincter 720 so as not to impair proper functioning of the sphincter 720 in controlling urine discharge. The connecting sutures 360 generally span the length of the urethra 715 surrounded by the external striated sphincter 720, so as to allow normal function of the sphincter 720. The bulbous urethral segment 375 is positioned within the urethra 715 proximal to the sphincter 720, also allowing for proper function of the sphincter 720.

In order to remove the stent 300 from the urethra 715, the urethra 715 is filled with local anesthetic gel. The retrieval suture 345 is gently but firmly pulled until the stent 300 is removed.

While the invention has been shown and described with reference to specific embodiments, it should be understood by those skilled in the art that various changes in form and detail may be made therein without departing from the spirit and scope of the invention.

The invention claimed is:

1. A stent comprising:
a first conduit defining a first lumen, a proximal end, and a distal end, the first conduit comprising a first malecot at the distal end comprising at least two members having at least one slit therebetween and in fluid communication with the first lumen, the first conduit further comprising a spring disposed within the first conduit and a second malecot at the proximal end comprising an enclosed annular structure surrounding and protruding from the first conduit, the enclosed annular structure being angled over the spring and disposed at an angle relative to the first conduit and pointed in a distal direction; and
a second conduit connected to the first conduit, the second conduit defining a second lumen, the second conduit comprising a third malecot comprising at least two members having at least one slit therebetween and in fluid communication with the second lumen.

2. The stent of claim 1 wherein the first malecot comprises a diameter larger than a diameter of the second malecot.

3. The stent of claim 1 wherein at least one of the first conduit, the first malecot, the second malecot, the second conduit, and the third malecot is formed from a material having a durometer value less then about 60 on a Shore A scale.

4. The stent of claim 1 wherein at least one of the first conduit, the first malecot, the second malecot, the second conduit, and the third malecot is formed from a material having a durometer value less than about 30 on a Shore A scale.

5. The stent of claim 1 wherein at least one of the first conduit, the first malecot, the second malecot, the second conduit, and the third malecot comprises a silicone polymer.

6. The stent of claim 1 wherein the at least two members of the first malecot are capable of folding such that the size of the at least one slit of the first malecot is larger when the at least two members of the first malecot are in a first position than when the at least two members of the first malecot are in a second position.

7. The stent of claim 1 wherein the second conduit is connected to the first conduit by at least one connector suture.

8. The stent of claim 1 wherein the spring is disposed within a wall of the first conduit.

* * * * *